(12) United States Patent
Sakanishi et al.

(10) Patent No.: US 8,273,921 B2
(45) Date of Patent: Sep. 25, 2012

(54) POLYGLYCEROL MONOETHER AND PROCESS FOR PRODUCING THE SAME

(75) Inventors: Yuichi Sakanishi, Ohtake (JP); Sunao Mihara, Ohtake (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 13/167,973

(22) Filed: Jun. 24, 2011

(65) Prior Publication Data

US 2011/0251437 A1    Oct. 13, 2011

Related U.S. Application Data

(62) Division of application No. 11/658,883, filed as application No. PCT/JP2005/015210 on Aug. 22, 2005, now abandoned.

(30) Foreign Application Priority Data

Aug. 30, 2004  (JP) ................................ 2004-250825
Apr. 26, 2005  (JP) ................................ 2005-127298

(51) Int. Cl.
   *C07C 43/00*   (2006.01)
(52) U.S. Cl. ........ 568/680; 568/579; 568/671; 568/672; 568/678
(58) Field of Classification Search .................... None
   See application file for complete search history.

(56) References Cited

U.S. PATENT DOCUMENTS

| | | | | |
|---|---|---|---|---|
| 4,298,764 A | * | 11/1981 | Berkowitz | ............ 568/618 |
| 4,465,866 A | * | 8/1984 | Takaishi et al. | ............ 568/618 |
| 5,708,108 A | | 1/1998 | Carey et al. | |

FOREIGN PATENT DOCUMENTS

| | | | |
|---|---|---|---|
| JP | 56-20534 | A | 2/1981 |
| JP | 57-197235 | A | 12/1982 |
| JP | 60-94126 | A | 5/1985 |
| JP | 6-293688 | A | 10/1994 |
| JP | 9-188755 | A | 7/1997 |
| JP | 9-235246 | A | 9/1997 |
| JP | 52-110617 | A | 9/1997 |
| JP | 2005-089494 | | 4/2005 |

OTHER PUBLICATIONS

Advisory Action issued Sep. 2, 2010 in U.S. Appl. No. 11/658,883.
Baskaran et al., "An Efficient and Steroselective Synthesis of (2R,2'S)-1-0-(2'-hydroxyhexadecyl)glycerol and its Oxo Analogs: Potential Antitumor Compounds from Shark Liver Oil," Tetrahedron Elsevier Science Publishers, Amsterdam, NL, vol. 52, No. 18, Apr. 29, 1996, pp. 6437-6452, XP004104133.
Burgess et al., "Synthesis of Linear 1-0-Dodecylglycerol Ethers Using Aliylglycidyl Ether As a Diglycerol Equivalent," Tetrahedron Letters, vol. 33, No. 28, 1992, pp. 4081-4082. XP002572019.
Engler et al., "Grenzliachenaktive Polyhydroxylverbindungen, XXIII, Alkylphenyl-polyglycerinather," Journal F. Prakt. Chemie, vol. 316, No. 2, 1974, pp. 325-336, XP002572018.
Erdlenbruch et al., "Transient and controllable opening of the blood-brain barrier to cytostatic and antibiotic agents by alkylglycerols in rats," Exp. Brain Research, vol. 135, 2000, pp. 417-422, XP002572021.
Office Action issued Jan. 4, 2010 in U.S. Appl. No. 11/658,883.
Office Action issued Jun. 23, 2010 in U.S. Appl. No. 11/658,883.
Office Action issued Mar. 24, 2011 in U.S. Appl. No. 11/658,883.
Office Action issued Oct. 9, 2009 in U.S. Appl. No. 11/658,883.
Sagitani et al., "Solution Properties of Homogeneous Polyglycerol Dodecyl Ether Nonionic Surfactants," JAOCS, vol. 66, No. 1, 1989, pp. 146-152, XP002572020.
Supplementary European Search Report issued on Mar. 24, 2010 in European Application 05780386.8.

* cited by examiner

*Primary Examiner* — Sudhakar Katakam
(74) *Attorney, Agent, or Firm* — Birch, Stewart, Kolasch & Birch, LLP

(57) ABSTRACT

A polyglycerol monoether is represented by FOLLOWING General Formula (1):

$$RO-(C_3H_6O_2)_n-H \qquad (1)$$

wherein R represents an alcohol residue having one to thirty carbon atoms; and "n" is an average number of moles of added glycerol units and represents a number of 2 or more, and has a content (peak area percentage) of monoether components of 75% or more and a content (peak area percentage) of diether components of 5% or less, as determined by reversed-phase partition high-performance liquid chromatography using a 80:20 (by volume) mixture of methanol and water as an eluent. The polyglycerol monoether may be prepared by adding a basic substance to an alcohol to yield an alkoxide, adding glycidol to the alkoxide, and subjecting them to a reaction at 0° C. to 100° C.

8 Claims, No Drawings

POLYGLYCEROL MONOETHER AND PROCESS FOR PRODUCING THE SAME

This application is a Divisional of U.S. application Ser. No. 11/658,883, filed on Jan. 30, 2007 now abandoned. U.S. application Ser. No. 11/658,883 is the National Phase application of International Application No. PCT/JP2005/015210, filed on Aug. 22, 2005, and claims the benefit of priority of Application No. 2004-250825, filed in Japan on Aug. 30, 2004, and Application No. 2005-127298, filed in Japan on Apr. 26, 2005. The entire contents of all of the above-identified applications are incorporated herein by reference.

BACKGROUND OF THE INVENTION

1. Technical Field

The present invention relates to polyglycerol monoethers and processes for producing the same. More specifically, it relates to polyglycerol monoethers of high quality, and processes for producing the same. Such polyglycerol monoethers are useful in areas of, for example, pharmaceutical drugs, foodstuffs, cosmetics and biochemistry.

2. Background Art

Polyglycerol monoethers such as polyglycerol monoalkyl ethers have been produced according to various processes. The processes include, for example, a process (1) in which 1 mole of epichlorohydrin is added to an alcohol, dehydrochlorination and ring-closing are carried out under basic conditions, and ring-opening is carried out with a diluted sulfuric acid, and these procedures are repeated until a target degree of polymerization is obtained. Polyglycerol monoethers obtained by this process, however, may be not suitable for use typically in foodstuffs, cosmetics, detergents or cleaning agents, because they may contain chlorine compounds and there remains some doubt about their safety. In addition, the process invites complicated reaction steps and high cost in order to produce a product having a high degree of polymerization, because a product having a single degree of polymerization alone is obtained according to the process.

Another process is a process (2) of adding glycidol to and polymerizing with an aliphatic alcohol (comparative examples of Japanese Unexamined Patent Application Publication (JP-A) No. Hei 9-188755). According to the process (2), glycidol can be surely added to a compound having a phenolic hydroxyl group, such as an alkylphenol, because of high reactivity of hydroxyl group. However, when glycidol and an aliphatic alcohol are subjected to reaction according to a regular procedure of this process, self-addition polymerization occurs, and this invites by-production of large quantities of impurities including unreacted aliphatic alcohol and polyglycerols. This is because the hydroxyl group in an aliphatic alcohol has low reactivity, and a glycidol molecule is added to a hydroxyl group of another glycidol molecule in the self-addition polymerization.

Yet another process is a process (3) of adding a hydroxyl-protected glycidol to an aliphatic alcohol and carrying out deprotection. Japanese Unexamined Patent Application Publication (JP-A) No. Hei 9-188755, for example, discloses a production process of reacting an aliphatic alcohol with a glycidyl ester, such as glycidyl acetate, in the presence of an alkali metal catalyst. Japanese Unexamined Patent Application Publication (JP-A) No. Hei 9-235246 discloses a production process of reacting an organic hydroxyl compound with benzyl glycidyl ether in the presence of a phase-transfer catalyst. These processes (3), however, carry out protection and deprotection of glycidol and are thereby complicated in procedures, although target compounds are obtained. In addition, these processes are not chemically and industrially safe when an acid hydride, for example, is used as a protecting reagent, because an acid formed in the system may invite an abnormal reaction.

Japanese Unexamined Patent Application Publication (JP-A) No. Sho 56-20534 discloses a process (4) of adding glycidol to an aliphatic alcohol in a nonpolar solvent such as xylene. According to the process (4), however, some doubt remains about the safety of a residual solvent in the resulting product, and the product may not be suitable for use in foodstuffs and cosmetics. In addition, this process is poor in productivity.

Japanese Unexamined Patent Application Publication (JP-A) No. Hei 6-293688 discloses a process (5) of reacting a polyhydroxy compound with an alkyl sulfate to yield a polyhydroxymonoalkyl ether. According to the process (5), however, there remains a considerable amount of unalkylated polyglycerols, and the polyglycerol monoalkyl ether may not sufficiently exhibit its original detergency. In addition to a monoalkyl compound, there is by-produced a considerable amount of a dialkyl compound, and this causes high crystallinity and low solubility in water.

Japanese Unexamined Patent Application Publication (JP-A) No. Sho 57-197235 discloses a process (6) of reacting an alkyl glycidyl ether with acetal or ketal of glycerol to synthetically form a 4-(2'-hydroxy-3'-alkoxy)propoxymethyl-1,3-dioxolane, and hydrolyzing this to thereby yield a 2-hydroxy-3-alkoxypropyl glyceryl ether. The resulting polyglycerol monoalkyl ether prepared according to the process (6), however, is expensive, and it is difficult to use the product as raw materials typically for foodstuffs.

As is described above, polyglycerol monoethers are known substances but have not been generally used, because they contain large amounts of impurities such as polyglycerols and dialkyl components and are high in production cost.

Analogous compounds which have been industrially used include polyglycerol mono(fatty acid) esters and polyoxyethylene monoalkyl ethers, and they are used in a variety of articles such as cosmetics and detergents or cleaning agents based on their activities. However, polyglycerol fatty acid esters are limited in use, because they are insufficient in resistance to hydrolysis, to salts, and to acids. Polyoxyethylene monoalkyl ethers may yield formaldehyde and are low in water-solubility. Such formaldehyde has been perceived as a problem. Accordingly, demands of the market have been made on replacements of these compounds.

Patent Document 1: Japanese Unexamined Patent Application Publication (JP-A) No. Hei 9-188755
Patent Document 2: Japanese Unexamined Patent Application. Publication (JP-A) No. Hei 9-235246
Patent Document 3: Japanese Unexamined Patent Application Publication (JP-A) No. Sho 56-20534
Patent Document 4: Japanese Unexamined Patent Application Publication (JP-A) No. Hei 6-293688
Patent Document 5: Japanese Unexamined Patent Application Publication (JP-A) No. Sho 57-197235

DISCLOSURE OF INVENTION

Problems to Be Solved by the Invention

An object of the present invention is to provide a high-quality polyglycerol monoether with little by-products. Another object of the present invention is to provide a process for efficiently producing this with safe.

Means for Solving the Problems

After intensive investigations to achieve the objects, the present inventors have found the objects may be achieved by adding a basic substance to an alcohol to form an alkoxide, and reacting the alkoxide with glycidol at specific temperatures in the production of a polyglycerol monoether by reacting an alcohol with glycidol. The present invention has been accomplished based on these findings.

Specifically, according to an embodiment of the present invention, there is provided a polyglycerol monoether represented by following, General Formula (1):

$$RO\text{—}(C_3H_6O_2)_n\text{—}H \quad (1)$$

wherein R represents an alcohol residue having one to thirty carbon atoms; and "n" is an average number of moles of added glycerol units and represents a number of 2 or more, in which the polyglycerol monoether has a content (peak area percentage) of monoether components of 75% or more and a content (peak area percentage) of diether components of 5% or less, as determined by reversed-phase partition high-performance liquid chromatography using a 80:20 (by volume) mixture of methanol and water as an eluent.

The polyglycerol monoether preferably has a content (peak area percentage) of polyglycerol components of 20% or less, as determined by reversed-phase partition high-performance liquid chromatography using a 80:20 (by volume) mixture of methanol and water as an eluent.

According to another embodiment of the present invention, there is provided a process for producing a polyglycerol monoether represented by following General Formula (1):

$$RO\text{—}(C3H6O2)n\text{—}H \quad (1)$$

wherein R represents an alcohol residue having one to thirty carbon atoms; and "n" is an average number of moles of added glycerol units and represents a number of 2 or more, the process including the steps of adding a basic substance to an alcohol to yield an alkoxide; adding glycidol to the alkoxide; and subjecting them to a reaction at 0° C. to 100° C.

In this production process, the reaction between the alkoxide and glycidol may be carried out, for example, at a temperature of 30° C. to 90° C. An alcohol having one to thirty carbon atoms may be used as the alcohol. The alcohol can also include at least one selected from the group consisting of allyl alcohol, lauryl alcohol, stearyl alcohol, sterols, tocols, and 2-ethylhexanol. The amount of glycidol is, for example, 0.1 to 40 moles per 1 mole of the alcohol. The basic substance may be at least one selected from the group consisting of lithium, sodium, potassium, and basic compounds containing these elements, and the amount thereof is, for example, 0.05 to 1.00 mole per 1 mole of the alcohol.

The term "alcohol residue" herein means a group corresponding to an alcohol, except for hydroxyl group. The term "alcohol(s)" includes alcohols, and phenols each having a hydroxyl group directly bound to an aromatic ring.

Advantages

A polyglycerol monoether according to the present invention is a high-quality polyglycerol monoether with little by-products and is suitable as a raw material typically for foodstuffs and cosmetics. A process according to the present invention can safely and efficiently produce a high-quality polyglycerol monoether with little by-products.

Best Mode For Carrying Out The Invention

The present invention relates to a high-quality polyglycerol monoether with little by-products, and to a process for producing a polyglycerol monoether. More specifically, it relates to a polyglycerol monoether having a content (peak area percentage) of monoether components of 75% or more and a content (peak area percentage) of diether components of 5% or less, as determined by reversed-phase partition high-performance liquid chromatography using a 80:20 (by volume) mixture of methanol and water as an eluent, and to a process for producing such a polyglycerol monoether. The polyglycerol monoether preferably has a content (peak area percentage) of polyglycerol components of 20% or less, as determined by reversed-phase partition high-performance liquid chromatography using a 80:20 (by volume) mixture of methanol and water as an eluent.

A polyglycerol ether according to the present invention is highly soluble in water and an aqueous solution thereof yields no deposited crystals of the polyglycerol ether even when the aqueous solution is left at room'temperature.

A polyglycerol monoether according to the present invention is a polyglycerol monoether represented by following General Formula (1):

$$RO\text{—}(C_3H_6O_2)_n\text{—}H \quad (1)$$

In General Formula (1), R represents an alcohol residue having one to thirty carbon atoms and is preferably one having six to twenty-one carbon atoms. The alcohol residue R includes aliphatic hydrocarbon groups such as straight- or branched-chain alkyl groups and alkenyl groups; monocyclic or polycyclic alicyclic hydrocarbon groups such as cycloalkyl groups; aromatic hydrocarbon groups; heterocyclic groups; and groups containing two or more of these groups combined with each other. These groups may each have one or more substituents.

In General Formula (1), "n" is an average number of moles of added constitutional repeating glycerol units (average degree of polymerization of glycerol). The average number "n" can be easily changed by varying the molar ratio of an alcohol to glycidol in a reaction. The average number "n" is 2 or more, more preferably 3 to 20, and further preferably 3 to 12. If "n" is less than 2, the resulting compound has poor solubility in water. In contrast, if "n" exceeds 20, the resulting compound may have excessively high water solubility and exhibit poor capability of reducing surface tension.

The unit in the parentheses in General Formula (1), represented by $C_3H_6O_2$, is a unit represented by following Formula (2) or (3). The compound may have both the two structures represented by Formulae (2) and (3) per one molecule.

$$\text{—}CH_2\text{—}CHOH\text{—}CH_2O\text{—} \quad (2)$$

$$\text{—}CH(CH_2OH)CH_2O\text{—} \quad (3)$$

A polyglycerol monoether according to the present invention has a content of the monoether components of 75% or more and has a content of diether components as impurities of 5% or less, as determined by the after-mentioned assay. The polyglycerol monoether preferably has a content of the monoether components of 90% or more and has a content of diether components as impurities of 1% or less. A polyglycerol ether having a content of monoether components of less than 75% and having a content of diether components exceeding 5% may have poor solubility in water.

A polyglycerol monoether according to the present invention has a content of polyglycerols as impurities of preferably 20% or less, and more preferably 10% or less, as determined by the after-mentioned assay. A polyglycerol monoether having a polyglycerol content exceeding 20% may have decreased foaming ability.

Next, a process for producing a polyglycerol monoether according to the present invention will be illustrated in detail. According to the present invention, a polyglycerol monoether such as a polyglycerol monoalkyl ether is prepared by adding a basic substance to a material alcohol (ROH) to form an alkoxide (including phenoxide), adding glycidol to the alkoxide, and carrying out a reaction between them at temperatures of 0° C. to 100° C. More specifically, a polyglycerol is obtained, for example, in the following manner. An alcohol is placed in a reactor, a basic substance is added to the alcohol to form an alkoxide, a reaction is carried out while adding glycidol, preferably in small portions, and the reaction mixture after the completion of reaction is, for example, neutralized by adding an acid to thereby yield a polyglycerol monoether.

Alcohols for use as raw materials are not limited, as long as they each have one to thirty carbon atoms. They include, for example, low molecular weight aliphatic alcohols such as methanol and ethanol; aliphatic alcohols having relatively large molecular weights, such as lauryl alcohol and 2-ethylhexanol; monocyclic or polycyclic alicyclic alcohols such as cyclohexanol and sterols; aromatic alcohols such as benzyl alcohol; phenols such as phenol; and dihydric or higher polyhydric alcohols and phenols. They can also be saturated aliphatic alcohols, unsaturated aliphatic alcohols, straight-chain aliphatic alcohols, and aliphatic alcohols having side chains.

Of these, preferred are alcohols having one to thirty carbon atoms, and more preferred are alcohols having six to twenty-one carbon atoms, of which aliphatic alcohols and monocyclic or polycyclic alicyclic alcohols are typically preferred. Representative examples of preferred alcohols include allyl alcohol, capryl alcohol, 2-ethylhexanol, lauryl alcohol, isotridecanol, myristyl alcohol, stearyl alcohol, isostearyl alcohol, behenol, ricinol, hydroxystearyl alcohol, sterols, and tocols. Of these typically preferred are allyl alcohol, lauryl alcohol, stearyl alcohol, sterols, tocols, and 2-ethylhexanol. Each of these alcohols can be used alone or in combination in a reaction.

Basic substances for use herein are preferably basic compounds that have high catalytic performance and whose remainders after the conversion of an alcohol into an alkoxide can be easily removed. Preferred basic substances include basic compounds corresponding to protic solvents such as water and alcohols, except with an alkali metal or alkaline earth metal cation replacing part of proton, such as sodium hydroxide, lithium hydroxide, potassium hydroxide, magnesium hydroxide, calcium hydroxide, sodium methoxide, sodium ethoxide, and sodium butoxide; basic compounds corresponding to saturated hydrocarbons, except with cation of an alkali metal or alkaline earth metal replacing a part thereof, such as butyllithium, methyllithium, and ethyllithium; and basic metals such as metal lithium, metal sodium, and metal potassium. Of basic substances, more preferred are lithium, sodium, potassium, and basic compounds containing these elements. Each of the basic substances can be used alone or in combination.

A basic substance is added to an alcohol before the addition of glycidol. The amount of a basic substance is, for example, 0.05 to 1.00 mole, and preferably 0.20 to 0.50 mole, per 1 mole of an alcohol. If the amount of a basic substance is less than the above-specified range, an alkoxide resides in a small amount in the system, and this invites self-polymerization of glycidol and thereby cause by-production of polyglycerols. If it is larger than the above-specified range, a base is in excess with respect to an alcohol, and this also invites self-polymerization of glycidol and thereby cause by-production of polyglycerols. The addition of a basic substance to a reaction system may be carried out in one step or in plural steps. After the addition of a basic substance, an alcohol is converted into an alkoxide where necessary with heating under normal pressure or heating under reduced pressure. This procedure may be carried out while distilling off by-produced water and other components, and the remainder of the basic substance.

The molar ratio of an alkoxide to glycidol is preferably such that the amount of glycidol is 0.1 mole to 40 moles per 1 mole of the alcohol. A reaction temperature is 0° C. to 100° C., preferably 30° C. to 90° C., and more preferably 40° C. to 70° C. If the reaction temperature is lower than 0° C., it is difficult to stir the composition during the reaction. If it exceeds 100° C., glycidol undergoes self-polymerization before it reacts with an alkoxide, to thereby cause by-production of polyglycerols. A low-boiling compound which does not react with glycidol or an inert solvent may be added upon reaction, so as to prevent elevation of a reaction temperature. A reaction is preferably carried out under flow of a dry inert gas, such as under flow of nitrogen gas, so as to ensure safety and to prevent hydrolysis of an alkoxide. If the system contains water, an alkoxide may undergo hydrolysis to thereby yield an alkaline compound, and this may act as an initiator and invite by-production of polyglycerols. The reaction can be carried out under a pressure (under a load) according to necessity.

After the completion of reaction, a base in a reaction product is neutralized with an acid, and salts are removed according to necessity. Thus, a polyglycerol monoether such as a polyglycerol monoalkyl ether is obtained. The acid herein includes an aqueous hydrochloric acid solution and an aqueous phosphoric acid solution. Neutralized salts such as phosphates can be separated and removed by filtration or centrifugation where necessary with the addition of a separation aid. A basic substance used as a reaction catalyst, and neutralized salts thereof can also be removed by ion-exchange resins.

The thus-obtained polyglycerol monoether can further be purified using various purification procedures according to necessity. Specific purification processes include, for example, (i) a deodorizing process in which heated, saturated steam (water vapor) is blown under reduced pressure to carry out steam deodorization, and (ii) a decoloring process such as bleaching using sodium hypophosphite or hydrogen peroxide. A product can also be naturally obtained without carrying out such a neutralization, desalting, and/or purification treatment.

The purity of a polyglycerol monoether according to the present invention may be analyzed typically by column chromatography and preferably by high-performance liquid chromatography (HPLC). The amounts and contents of polyglycerol monoethers, and by-products including polyglycerols and polyglycerol diethers can be determined based on peak area ratios.

Solid phases for use in high-performance liquid chromatography include reversed-phase partition column packings using, as a carrier, silica gel having octadecylsilyl group, octylsilyl group, butylsilyl group, trimethylsilyl group, and/or phenylsilyl group as a functional group; ordinary phase partition column packings using, as a carrier, silica gel having cyanopropyl group and/or aminopropyl group as a functional group; ion-exchange column packings having quaternary ammonium group and/or phenylsulfonic group as a functional group; and adsorptive column packings containing a porous silica gel. Among them, preferred are reversed-phase partition column packings using, as a carrier, a silica gel having octadecylsilyl (ODS) group. Columns preferably have dimensions of at least 4.6 mm in diameter and 250 mm in length for higher separation performance. Such columns are more preferably arranged in series for further higher separation performance.

The content of monoether components (polyglycerol monoethers), the content of diether components (polyglycerol diethers), and the content of polyglycerols as specified in the present invention are measurements (peak area percentages) as determined by reversed-phase partition high-performance liquid chromatography using a 80:20 (by volume) mixture of methanol and water as an eluent.

EXAMPLES

The present invention will be illustrated in further detail with reference to several examples below, which by no means limit the scope of the present invention. In the following examples and comparative examples, products were eluted using high-performance liquid chromatography, were detected with a refractive index detector (RI), and peak areas of individual components were determined. Thus, the contents of monoalkyl components (polyglycerol monoalkyl ethers), dialkyl components (polyglycerol dialkyl ethers), and polyglycerols are indicated in terms of area percentages.

(Analysis Conditions of High-performance Liquid Chromatography)

High-performance liquid chromatograph main body: Waters 2690 (Waters Corporation)

Column: Wakosil 5C18, two columns (Wako Pure Chemical Industries, Ltd.; reversed-phase partition columns having octadecylsilyl group as a functional group)

Eluent: methanol/water (=80/20 (by volume))

Flow rate: 0.5 ml/min

Temperature of column oven: 40° C.

Detector: refractive index detector (differential refractometer)

Sample concentration: 10% (the same as the ratio of solvent to eluent)

Sample amount: 10 μl

Polyglycerols have retention times of less than six minutes, polyglycerol monolauryl ethers have retention times of six minutes to twenty-five minutes, and polyglycerol dilauryl ethers have retention times of twenty-five minutes to thirty-five minutes. The detection limit of dialkyl components is 0.05%.

Example 1

In a four-neck flask were placed 184.3 g (1.0 mol) of lauryl alcohol and 8.0 g (0.2 mol) of sodium hydroxide. Next, the reaction system was decompressed to a pressure of 30 mmHg (3990 Pa) using an aspirator while heating at 80° C. for ninety minutes, in order to remove water in the reaction system. The reaction system was recovered to normal atmospheric pressure, and 222.2 g (3.0 mol) of glycidol was added dropwise to the sufficiently stirred reaction mixture under nitrogen flow over twelve hours while maintaining the reaction temperature to 70° C. The reaction mixture was then neutralized with an aqueous phosphoric acid solution to a pH of 7, and low-boiling components were distilled off by decompressing the reaction system to a pressure of 1 mmHg (133 Pa) with heating again to 200° C. A neutralized residue of the base catalyst was removed by centrifugation. The resulting product was analyzed and was found to have a content of monoalkyl components (n=4) of 95.1%, a content of dialkyl components of equal to or lower than the detection limit, and a content of polyglycerol components of 4.9%.

Example 2

In a four-neck flask were placed 184.3 g (1.0 mol) of lauryl alcohol and 4.8 g (0.2 mol) of lithium hydroxide. Next, the reaction system was decompressed to a pressure of 30 mmHg (3990 Pa) using an aspirator while heating at 80° C. for ninety minutes, in order to remove water in the reaction system. The reaction system was recovered to normal atmospheric pressure, and 222.2 g (3.0 mol) of glycidol was added dropwise to the sufficiently stirred reaction mixture under nitrogen flow over twelve hours while maintaining the reaction temperature to 70° C. The reaction mixture was then neutralized with an aqueous phosphoric acid solution to a pH of 7, and low-boiling components were distilled off by decompressing the reaction system to a pressure of 1 mmHg (133 Pa) with heating again to 200° C. A neutralized residue of the base catalyst was removed by centrifugation. The resulting product was analyzed and was found to have a content of monoalkyl components (n=4) of 95.9%, a content of dialkyl components of equal to or lower than the detection limit, and a content of polyglycerol components of 4.1%.

Example 3

In a four-neck flask were placed 116.2 g (1.0 mol) of 2-ethylhexanol and 8.0 g (0.2 mol) of sodium hydroxide. Next, the reaction system was decompressed to a pressure of 30 mmHg (3990 Pa) using an aspirator while heating at 80° C. for ninety minutes, in order to remove water in the reaction system. The reaction system was recovered to normal atmospheric pressure, and 222.2 g (3.0 mol) of glycidol was added dropwise to the sufficiently stirred reaction mixture under nitrogen flow over twelve hours while maintaining the reaction temperature to 50° C. The reaction mixture was then neutralized with an aqueous phosphoric acid solution to a pH of 7, and low-boiling components were distilled off by decompressing the reaction system to a pressure of 1 mmHg (133 Pa) with heating again to 200° C. A neutralized residue of the base catalyst was removed by centrifugation. The resulting product was analyzed and was found to have a content of monoalkyl components (n=4) of 92.9%, a content of dialkyl components of equal to or lower than the detection limit, and a content of polyglycerol components of 7.1%.

Example 4

In a four-neck flask were placed 184.3 g (1.0 mol) of lauryl alcohol and 16.8 g (0.3 mol) of potassium hydroxide. Next, the reaction system was decompressed to a pressure of 30 mmHg (3990 Pa) using an aspirator while heating at 80° C. for ninety minutes, in order to remove water in the reaction system. The reaction system was recovered to normal atmospheric pressure, and 222.2 g (3.0 mol) of glycidol was added dropwise to the sufficiently stirred reaction mixture over twelve hours under nitrogen flow while maintaining the reaction temperature to 70° C. The reaction mixture was then neutralized with an aqueous phosphoric acid solution to a pH of 7, and low-boiling components were distilled off by decompressing the reaction system to a pressure of 1 mmHg (133 Pa) with heating again to 200° C. A neutralized residue of the base catalyst was removed by centrifugation. The resulting product was analyzed and was found to have a content of monoalkyl components (n=4) of 83.4%, a content of dialkyl components of equal to or lower than the detection limit, and a content of polyglycerol components of 16.6%.

Comparative Example 1

In a four-neck flask were placed 184.3 g (1.0 mol) of lauryl alcohol and 16.8 g (0.3 mol) of potassium hydroxide. Next, the reaction system was decompressed to a pressure of 30 mmHg (3990 Pa) using an aspirator while heating at 80° C. for ninety minutes, in order to remove water in the reaction system. The reaction system was recovered to normal atmospheric pressure, and 222.2 g (3.0 mol) of glycidol was added dropwise to the sufficiently stirred reaction mixture over twelve hours under nitrogen flow while maintaining the reaction temperature to 130° C. The reaction mixture was then neutralized with an aqueous phosphoric acid solution to a pH of 7, and low-boiling components were distilled off by decompressing the reaction system to a pressure of 1 mmHg (133 Pa) with heating again to 200° C. A neutralized residue of the base catalyst was removed by centrifugation. The resulting product was analyzed and was found to have a content of monoalkyl components (n=4) of 65.6%, a content of dialkyl components of equal to or lower than the detection limit, and a content of polyglycerol components of 34.4%.

Comparative Example 2

In a four-neck flask were placed 116.2 g (1.0 mol) of 2-ethylhexanol and 16.8 g (0.3 mol) of potassium hydroxide. Next, the reaction system was decompressed to a pressure of 30 mmHg (3990 Pa) using an aspirator while heating at 80° C. for ninety minutes, in order to remove water in the reaction system. The reaction system was recovered to normal atmospheric pressure, and 222.2 g (3.0 mol) of glycidol was added dropwise to the sufficiently stirred reaction mixture under nitrogen flow over twelve hours while maintaining the reaction temperature to 130° C. The reaction mixture was then neutralized with an aqueous phosphoric acid solution to a pH of 7, and low-boiling components were distilled off by decompressing the reaction system to a pressure of 1 mmHg (133 Pa) with heating again to 200° C. A neutralized residue of the base catalyst was removed by centrifugation. The resulting product was analyzed and was found to have a content of monoalkyl components (n=4) of 51.9%, a content of dialkyl components of equal to or lower than the detection limit, and a content of polyglycerol components of 48.1%.

Comparative Example 3

In a 1-liter four-neck reactor was placed 314.3 g (1 mol) of tetraglycerol (Daicel Chemical Industries, Ltd., PGL 04). With stirring and heating at 130° C., 12 g (0.3 mol) of sodium hydroxide (NaOH) was dissolved in tetraglycerol over five hours. Next, the reaction system was decompressed to a pressure of 30 mmHg (3990 Pa) using an aspirator while heating at 130° C. for two hours, in order to remove water in the reaction system. The reaction system was recovered to normal atmospheric pressure, and 86.5 g (0.3 mol) of sodium lauryl sulfate was added to the sufficiently stirred reaction mixture over eight hours under nitrogen flow while maintaining the reaction system to 130° C. The mixture was further heated and stirred at 180° C. for seven hours. The reaction mixture was then neutralized with an aqueous phosphoric acid solution to a pH of 7, and a neutralized residue of the base catalyst was removed by centrifugation. The resulting product was analyzed and was found to have a content of monoalkyl components (n=4) of 14.6%, a content of dialkyl components of 7.2%, and a content of polyglycerol components of 61.6%.

Comparative Example 4

In a 1-liter four-neck reactor were placed 314.3 g (1 mol) of tetraglycerol (Daicel Chemical Industries, Ltd., PGL 04). Tetraglycerol was then combined with 80 g of a 50% sodium hydroxide solution, and the mixture was heated to 120° C. with dehydration. After cooling the reaction mixture to 100° C., 204.8 g (1 mol) of 1-chlorododecane was added dropwise to the sufficiently stirred reaction mixture under nitrogen flow over an hour and a half. The reaction mixture was then neutralized with an aqueous phosphoric acid solution to a pH of 7, and a neutralized residue of the base catalyst was removed by centrifugation. The resulting product was analyzed and was found to have a content of monoalkyl components (n=4) of 35.1%, a content of dialkyl components of 22.5%, and a content of polyglycerol components of 31.2%.

Comparative Example 5

In a 1-liter four-neck reactor was placed 314.3 g (1 mol) of tetraglycerol (Daicel Chemical Industries, Ltd., PGL 04). With stirring and heating at 130° C., 12 g (0.3 mol) of sodium hydroxide (NaOH) was dissolved in tetraglycerol over five hours. Next, the reaction system was decompressed to a pressure of 30 mmHg (3990 Pa) using an aspirator while heating at 130° C. for two hours, in order to remove water in the reaction system. The reaction system was recovered to normal atmospheric pressure, and 228.4 g (1.0 mol) of lauryl glycidyl ether was added dropwise to the sufficiently stirred reaction mixture over eight hours under nitrogeti flow while maintaining the reaction system td 130° C. The mixture was further stirred for seven hours while maintaining the temperature to 130° C. The reaction mixture was then neutralized with an aqueous phosphoric acid solution to a pH of 7, and a neutralized residue of the base catalyst was removed by centrifugation. The resulting product was analyzed and was found to have a content of monoalkyl components (n=4) of 48.6%, a content of dialkyl components of 12.2%, and a content of polyglycerol components of 28.6%.

Industrial Applicability

A polyglycerol monoether according to the present invention is a high-quality polyglycerol monoether with little by-products and is suitable as a raw material for foodstuffs and cosmetics. A process according to the present invention can safely and efficiently produce a high-quality polyglycerol monoether with little by-products. A polyglycerol monoether with little by-produced polyglycerols obtained according to the present invention is superior in resistance to hydrolysis, safety, and water-solubility to polyglycerol fatty acid esters and polyoxyethylene alkyl ethers, is inexpensive, and can be used typically as an emulsifier or a base material in a wide variety of areas such as foodstuffs, cosmetics, and pharmaceutical drugs. When it is used, for example, as a surfactant or emulsion stabilizer, it is expected for exhibiting functions equivalent to or higher than polyglycerol fatty acid esters and polyoxyethylene alkyl ethers.

The invention claimed is:

1. A process for producing a polyglycerol monoether represented by following General Formula (1):

$$RO-(C_3H_6O_2)_n-H \qquad (1)$$

wherein R represents an alcohol residue having one to thirty carbon atoms; and n is an average number of moles of added glycerol units and represents a number of 2 or more, the process comprising the steps of adding a basic substance to an alcohol to yield an alkoxide; adding glycidol to the alkoxide; and subjecting them to a reaction at 0° C. to 100° C., wherein the alcohol converts into the alkoxide with heating while distilling off by-produced water.

2. The process for producing a polyglycerol monoether according to claim 1, further comprising carrying out the reaction between the alkoxide and glycidol at a temperature of 30° C. to 90° C.

3. The process for producing a polyglycerol monoether according to claim 1, further comprising using an alcohol having one to thirty carbon atoms as the alcohol.

4. The process for producing a polyglycerol monoether according to claim 1, further comprising using at least one selected from the group consisting of allyl alcohol, lauryl alcohol, stearyl alcohol, sterols, tocols, and 2-ethylhexanol as the alcohol.

5. The process for producing a polyglycerol monoether according to claim 1, further comprising using 0.1 to 40 moles of glycidol per 1 mole of the alcohol.

6. The process for producing a polyglycerol monoether according to claim 1, further comprising using, as the basic substance, at least one selected from the group consisting of lithium, sodium, potassium, and basic compounds containing them in an amount of 0.05 to 1.00 mole per 1 mole of the alcohol.

7. The process for producing a polyglycerol monoether according to claim 1, wherein the average number n is 3 to 20.

8. The process for producing a polyglycerol monoether according to claim 1, further comprising using at least one selected from the group consisting of allyl alcohol, stearyl alcohol, sterols, tocols, and 2-ethylhexanol as the alcohol.

\* \* \* \* \*